United States Patent
Kahn et al.

(10) Patent No.: US 11,972,775 B1
(45) Date of Patent: Apr. 30, 2024

(54) DETERMINATION OF SLEEP PARAMETERS IN AN ENVIRONMENT WITH UNCONTROLLED NOISE SOURCES

(71) Applicants: Philippe Richard Kahn, Santa Cruz, CA (US); Sonia Lee Kahn, Santa Cruz, CA (US); Arthur Kinsolving, Santa Cruz, CA (US); Mark Andrew Christensen, Santa Cruz, CA (US); Venkat Easwar, Los Gatos, CA (US)

(72) Inventors: Philippe Richard Kahn, Santa Cruz, CA (US); Sonia Lee Kahn, Santa Cruz, CA (US); Arthur Kinsolving, Santa Cruz, CA (US); Mark Andrew Christensen, Santa Cruz, CA (US); Venkat Easwar, Los Gatos, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

(21) Appl. No.: 17/936,844

(22) Filed: Sep. 29, 2022

Related U.S. Application Data

(63) Continuation of application No. 16/949,124, filed on Oct. 14, 2020, now Pat. No. 11,462,238.

(60) Provisional application No. 62/915,006, filed on Oct. 14, 2019.

(51) Int. Cl.
*G10L 21/0216* (2013.01)
*G10L 15/20* (2006.01)
*G10L 25/66* (2013.01)

(52) U.S. Cl.
CPC .............. *G10L 25/66* (2013.01); *G10L 15/20* (2013.01)

(58) Field of Classification Search
CPC ........... G10L 21/0208; G10L 21/02085; G10L 21/0216; G10L 25/66; A61B 5/4806; A61B 5/4809; A61B 5/4815
USPC .......... 704/226, 227, 228, 270, 215; 600/529
See application file for complete search history.

(56) References Cited

U.S. PATENT DOCUMENTS

| | | | |
|---|---|---|---|
| 6,320,968 B1 * | 11/2001 | Linder | G10L 21/02 381/94.1 |
| 9,161,719 B2 * | 10/2015 | Tsutsumi | A61B 7/003 |
| 9,870,719 B1 * | 1/2018 | Watkins | G10L 25/21 |
| 9,905,118 B1 * | 2/2018 | Vanchev | G08B 29/02 |
| 9,990,026 B1 | 6/2018 | Kahn et al. | |
| 10,084,423 B1 * | 9/2018 | Goldstein | G10L 25/84 |

(Continued)

FOREIGN PATENT DOCUMENTS

WO    WO-2022076670 A1 *    4/2022    ............ A61M 21/00

OTHER PUBLICATIONS

Final Office Action, U.S. Appl. No. 16/949,124, dated Mar. 18, 2022, 24 pages.

(Continued)

*Primary Examiner* — Martin Lerner
(74) *Attorney, Agent, or Firm* — Nicholson De Vos Webster & Elliott LLP; Judith Szepesi

(57) ABSTRACT

The present system ensures that external noise sources do not taint sensor data recorded about a user's sleep parameters, to reduce false positives and false negatives, and provides a more accurate record of the user's sleep sounds, by cycling on and off noise sources. Additionally, the present system, in one embodiment, may be used to track changes in sound patterns from the user and from the environment. This may lead to early warning of health issues, as well as issues with the devices in the bedroom.

20 Claims, 7 Drawing Sheets

(56) References Cited

U.S. PATENT DOCUMENTS

| | | | |
|---|---|---|---|
| 10,542,930 B1* | 1/2020 | Sanchez | A61B 5/4818 |
| 10,657,968 B1 | 5/2020 | Raman | |
| 10,791,986 B1 | 10/2020 | Kahn et al. | |
| 10,921,763 B1 | 2/2021 | Correnti et al. | |
| 11,462,238 B2* | 10/2022 | Kahn | A61B 5/4806 |
| 2008/0275349 A1 | 11/2008 | Halperin et al. | |
| 2008/0281586 A1 | 11/2008 | Florencio et al. | |
| 2010/0302044 A1 | 12/2010 | Chacon et al. | |
| 2011/0046488 A1 | 2/2011 | Elle et al. | |
| 2011/0082575 A1 | 4/2011 | Muesch | |
| 2012/0197612 A1* | 8/2012 | Drews | G01H 3/10 |
| | | | 702/199 |
| 2012/0237056 A1* | 9/2012 | Emlinger | H04B 15/005 |
| | | | 381/94.5 |
| 2013/0234823 A1 | 9/2013 | Kahn et al. | |
| 2015/0302854 A1 | 10/2015 | Clough | |
| 2015/0326748 A1* | 11/2015 | Tisch | H04R 3/005 |
| | | | 348/231.4 |
| 2016/0221583 A1 | 8/2016 | Valeri et al. | |
| 2018/0125256 A1 | 5/2018 | Tsern et al. | |
| 2019/0090860 A1 | 3/2019 | Shinar et al. | |
| 2019/0259370 A1 | 8/2019 | Yamaguchi et al. | |
| 2019/0272813 A1 | 9/2019 | Stickney et al. | |
| 2020/0090676 A1 | 3/2020 | Nandi et al. | |
| 2020/0261687 A1 | 8/2020 | Kremer et al. | |
| 2022/0211322 A1* | 7/2022 | Gunderson | A61B 5/4809 |

OTHER PUBLICATIONS

Non-Final Office Action, U.S. App. No. 16/949, 124, dated Dec. 2, 2021, 20 pages.

Notice of Allowance, U.S. Appl. No. 16/949,124, dated Jun. 1, 2022, 9 pages.

Requirement for Restriction/Election, U.S. Appl. No. 16/949,124, dated Sep. 14, 2021, 8 pages.

* cited by examiner

DETERMINATION OF SLEEP PARAMETERS IN AN ENVIRONMENT WITH UNCONTROLLED NOISE SOURCES

RELATED APPLICATION

The present application claims priority as a continuation of U.S. patent application Ser. No. 16/949,124, filed Oct. 14, 2020, issuing as U.S. Pat. No. 11,462,238 on Oct. 4, 2022, which application claims priority to U.S. Provisional Application 62/915,006, filed on Oct. 14, 2019, both of which are incorporated in their entirety by reference.

FIELD

The present invention relates to sleep, and more particularly to detecting sleep sounds such as snoring and apneas in a noisy environment.

BACKGROUND

Modern beds are much improved from being wooden slabs upon which mattresses may be placed. A modern bed may be adjustable in configuration, with the ability to move the head and/or foot portion of the mattress to different positions. Modern beds may also include various heaters, power supplies, fans, and other elements to enable such improvements. Additionally, modern bedrooms are also noisy environments, with everything from white noise machines, to fans, to heaters, and other sources of noise and vibration.

BRIEF DESCRIPTION OF THE FIGURES

The present invention is illustrated by way of example, and not by way of limitation, in the figures of the accompanying drawings and in which like reference numerals refer to similar elements and in which:

FIG. 7A illustrates an exemplary signal from a piezoelectric sensor with a bed fan turned on.

DETAILED DESCRIPTION

Figure 1:
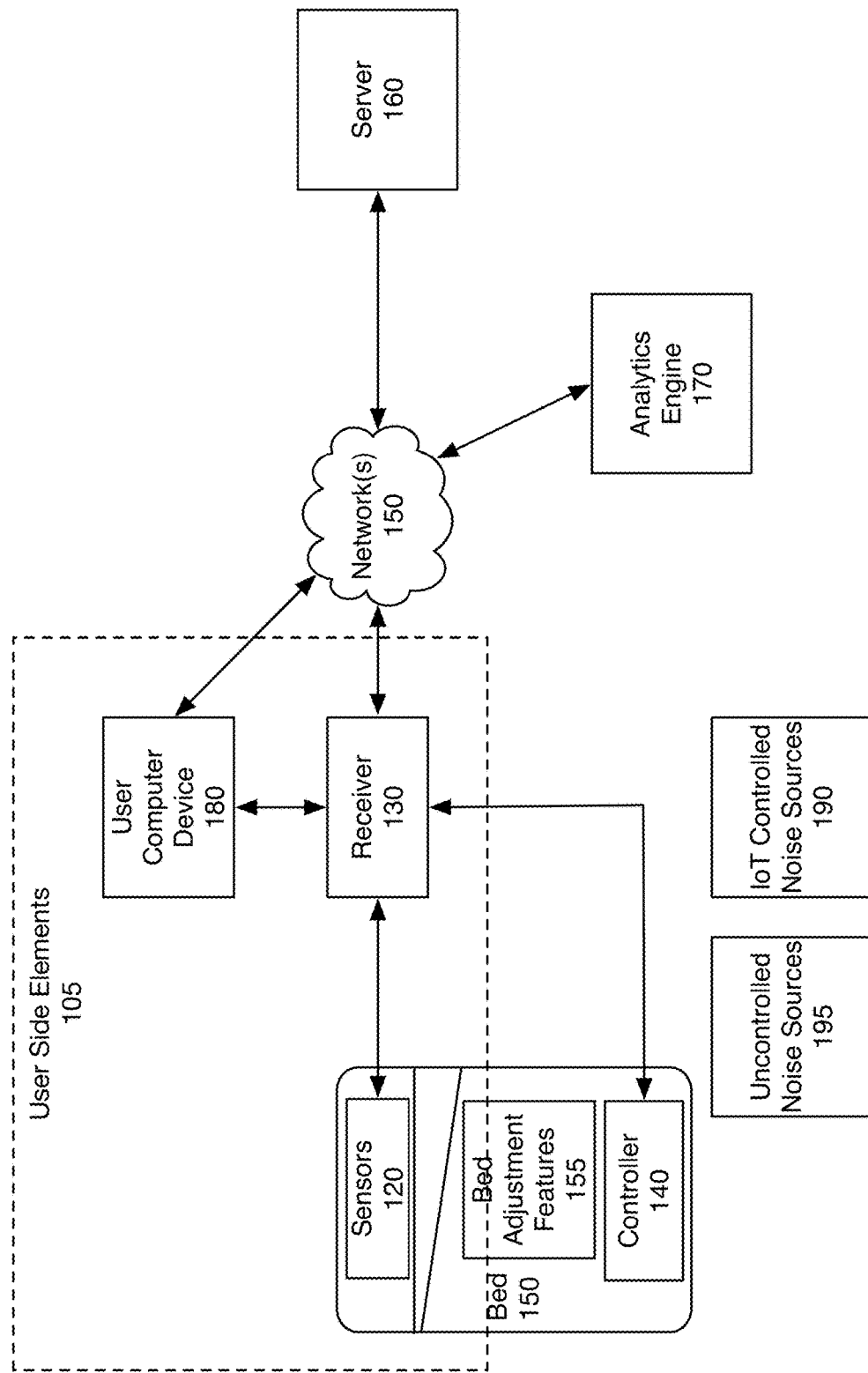
FIG. 1 is a block diagram of one embodiment of the environment in which the improved sleep noise detection system may be used.

One way to analyze sleep is to utilize one or more sensors in a bed, or associated with a bed, to detect user motion and/or user noises. In one embodiment, a piezoelectric sensor may be placed under a mattress to detect such motions. The data from the piezoelectric sensor may be analyzed, in one embodiment in accordance with co-pending application U.S. application Ser. No. 16/601,567 entitled "Sleep Detection and Analysis System," filed on Oct. 14, 2019 (Our Ref. 8689P233), and incorporated herein by reference. Although the piezoelectric sensor senses tiny motions and vibrations, the data may be analyzed to identify respiration as well as sleep sounds. Sleep sounds, in this context refers to incidents of apnea and snoring. Although the term "sleep sound" is used, the detection of such sounds may be accomplished through analysis of motion data, rather than microphone recording, in one embodiment. In another embodiment, data from a microphone and from motion sensors may be combined to detect sleep sounds.

However, in a modern bedroom, there are a large number of noise sources, including fans and motors within the bed itself, external IoT controlled devices, external controlled devices such as air conditioners and heaters, and uncontrolled noise sources. In one embodiment, this is particularly acute for smart beds, which provide heating and cooling built into the bed itself, creating in-situ noise sources. Noise, in this context, encompasses not just sounds but also vibrations and other motions which are imparted to the sleeping area by external devices and environmental effects rather than the user's respiration and heartbeat. When using the sensor system detecting motion, vibration, and/or sound, noise sources may cause false positives (indications of problematic sleep sounds when there are none) and false negatives (failure to detect sleep sounds when they are present, due to the noise).

The present system ensures that such external noise sources do not taint the data, to reduce false positives and false negatives, and provides a more accurate record of the user's sleep sounds. Additionally, the present system, in one embodiment, may be used to track changes in sound patterns from the user and from the environment. This may lead to early warning of health issues, as well as issues with the devices in the bedroom.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized, and that logical, mechanical, electrical, functional, and other changes may be made without departing from the scope of the present invention. The following detailed description is, therefore, not to be taken in a limiting sense, and the scope of the present invention is defined only by the appended claims.

FIG. 1 is a block diagram of one embodiment of the environment in which the improved sleep noise detection system may be used. The system includes a sleep analytics system including sensors 120, receiver 130, server 160, and analytics engine 170. In one embodiment, the client portion 105 of the sleep analytics system is located in a user's home and includes the sensors 120 and receiver 130.

In one embodiment, the receiver 130 is coupled to sensors 120 in the bed 150 via a cable. In another embodiment the connection may be wireless, such as low power Bluetooth (BLE), Wi-Fi, or another type of wireless connection. In one embodiment, receiver 130 also may be coupled to a controller 140, which controls bed 150. In one embodiment, this connection is a wired connection. Alternatively, it may be a wireless connection.

In one embodiment, the sensors 120 may include one or more sensors positioned in bed 150 which are used to measure the user's sleep parameters, which in one embodiment includes sleep phase, heartbeat, and respiration including respiratory events. In one embodiment, sensors 120 may include sensors which are not in bed 150 but positioned in the room in which the bed 150 is located. In one embodiment, one or more these additional sensors may be built into receiver 130. In one embodiment, there may be external sensors which may be coupled to receiver 130 either via wires or wirelessly. The receiver 130 collects data from the one or more sensors, for transmission to the server 160.

In one embodiment, the bed 150 may be a smart bed including bed adjustment features 155, such as air conditioners, heaters, fans, and other heating and/or cooling systems, as well as motors and other position adjustment elements. In one embodiment, controller 140 controls these bed adjustment features 155. These bed adjustment features 155 however impart noise to the system, which may impact the ability of sensors 120 to accurately evaluate the user's sleep. In addition to the bed adjustment features 155, other noise sources may be IoT controlled noise sources 190, and uncontrolled noise sources 195. An IoT controlled noise source, for example, may be a network connected room heating or air conditioning system, white noise machine, or other sources of vibration or noise in the room which may be controlled remotely via a network. Uncontrolled noise sources 195 may be those sources which cannot be controlled via a network, which may include non-networked heating or air conditioning system, white noise machine, or other sources of vibration or noise in the room. Additionally, uncontrolled noise sources 195 may include external noise sources such as vehicles driving by, birds or other animal noises, noise from nearby residences or commercial facilities, and other neighborhood noises. In one embodiment, the present system attempts to address the impact of all of these noise sources on the sensor data, to provide a more accurate reflection of the user's sleep parameters, including respiratory incidents.

In one embodiment, the receiver 130 is coupled to the server 160 via a network 150. The server portion includes server 160 and analytics engine 170, which in one embodiment are located off-site, removed from the user. In another embodiment, the server may be a local system, such as a computer system running an application. The network 150 may be the Internet, and the receiver 130 may send data to the server via a wireless network, such as Wi-Fi or the cellular network. In one embodiment, server 160 and analytics engine 170 may be on the same physical device. In one embodiment, server and/or analytics engine 170 may include a plurality of devices. In one embodiment, one or both of the server 170 and the analytics engine 170 may be using cloud computing and may be implemented as a distributed system. In one embodiment, a portion of the analytics and/or preprocessing of the data may be performed on the receiver 130 and/or user computer device 180, while another portion may be done on remote analytics engine 170.

Figure 2:
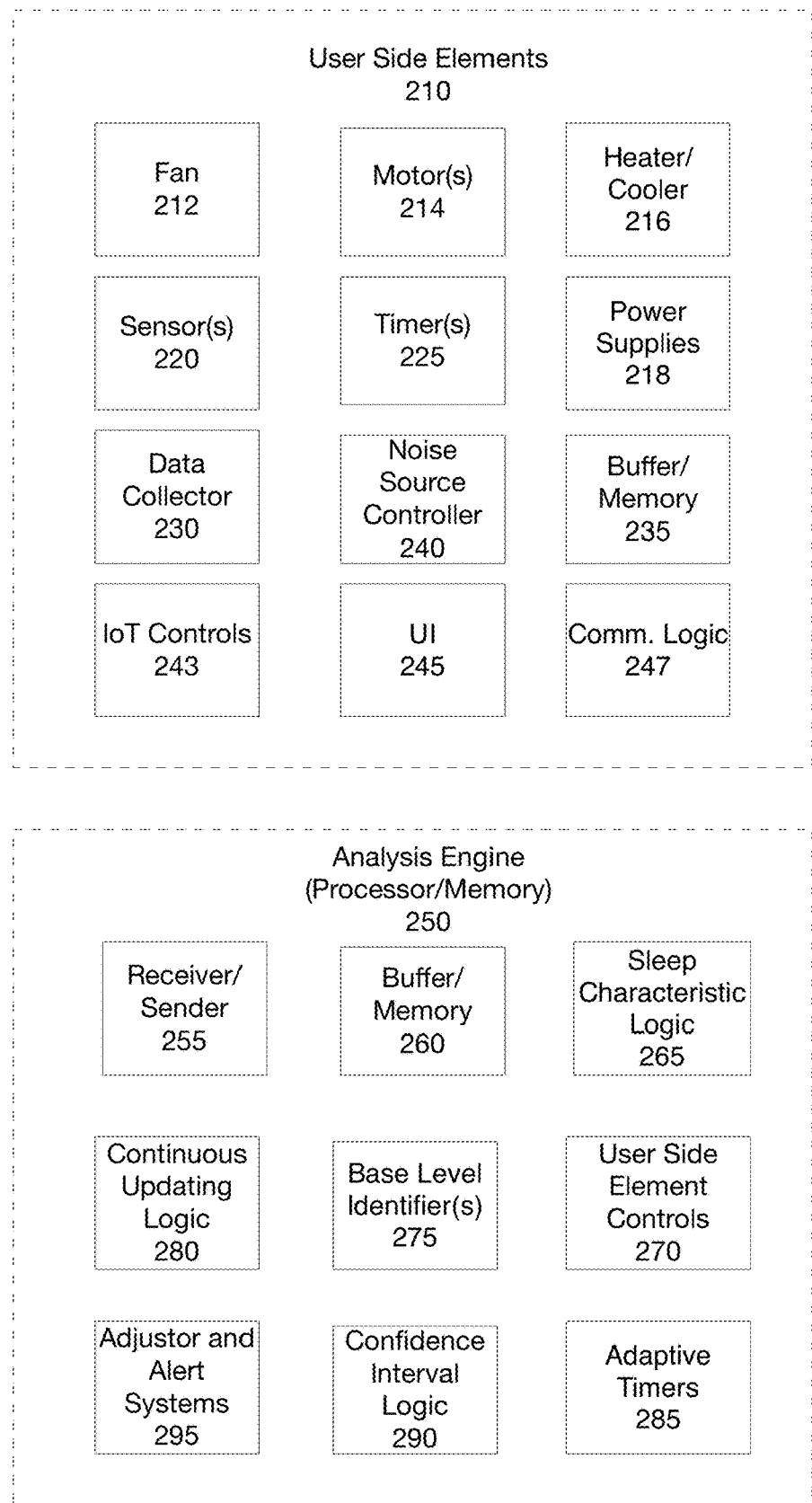
FIG. 2 is a block diagram of one embodiment of the sleep noise detection system.

FIG. 2 is a block diagram of one embodiment of the sleep noise detection system. The user side elements 210 in one embodiment may be included in the bed, receiver, and user environment, as discussed above. The analysis engine 250 may be implemented in a server, including a processor and memory. In one embodiment the server may be a cloud-based server where the processing is performed by one or more distributed processors, and the data is stored in a cloud data structure. However, the detectors, logics, and controls of the analysis engine 250 are implemented by a processing system.

The user side elements 210 can include one or more of fans 212, motors 214, heaters/coolers 216, power supplies 218. These elements are present in smart beds, to provide controls for comfort and to improve sleep.

User side elements 210 further include in one embodiment one or more sensors 220. The sensors 220, in one embodiment, include a motion sensor. The motion sensor may be a piezoelectric pressure sensor. The sensors may further include a temperature sensor, a microphone to detect audio data, a humidity sensor, light sensor, and other sensors. Sensors 220 may be embedded within the bed frame, a mattress, in a sensor pod positioned under or over the mattress, or off the bed. In one embodiment, sensors 220 may be distributed in multiple locations.

Timers 225 control the timing of various actions, and in one embodiment, control the periodic sensing, data processing, and other activities as will be described below.

Data collector 230 in one embodiment collects data from the various sensors and controlled devices. In one embodiment, the data collector 230 pre-processes the data so that pre-processed data is sent to the analysis engine 250. In one embodiment, data collector 230 receives data from a plurality of sensors and devices, each with a time stamp. In one embodiment, data collector 230 combines the data from the plurality of sensors and devices. The data is stored in the buffer/memory 235, in one embodiment.

Noise source controller 240 in one embodiment controls the controllable noise sources, which include noise sources such as the fans 212, motors 214, heater/coolers 216, and other portions of the bed, as well as external noise sources which can be controlled via a network. In one embodiment, for external noise sources, the noise source controller 240 interfaces with IoT (internet of things) controls 243. The noise source controller 240 may turn off noise sources periodically, or in response to a detection of an event, as will be described below.

Figure 7A:
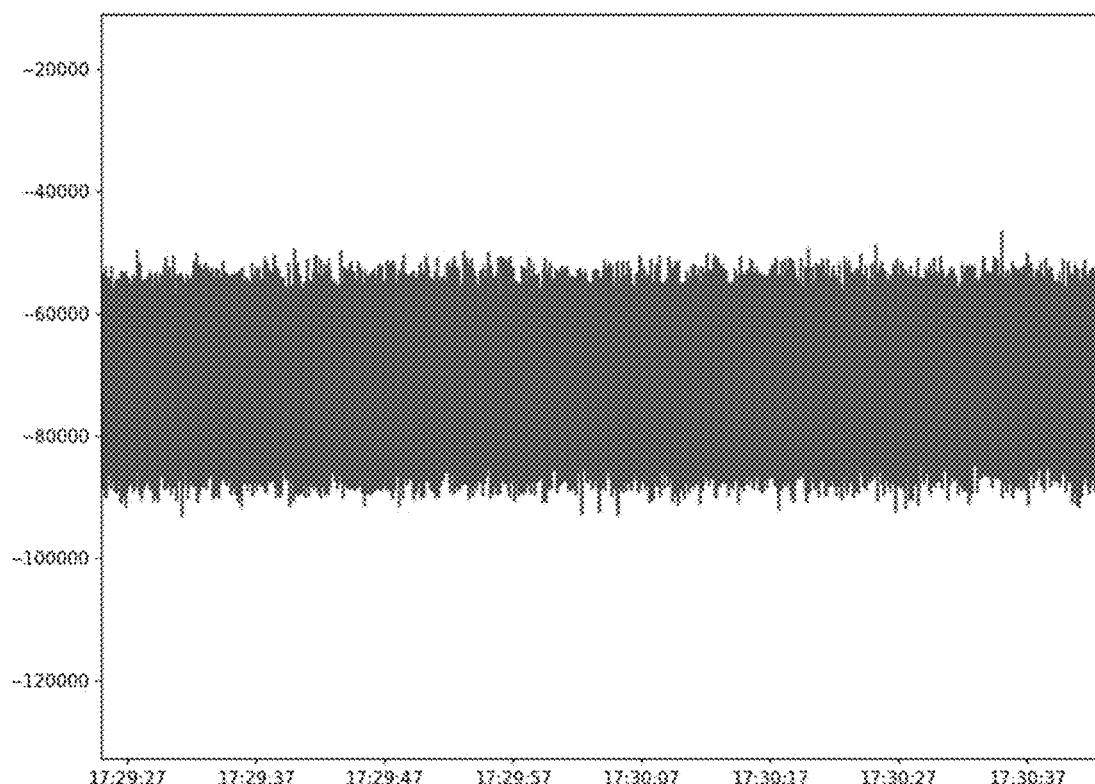
Figure 7B:
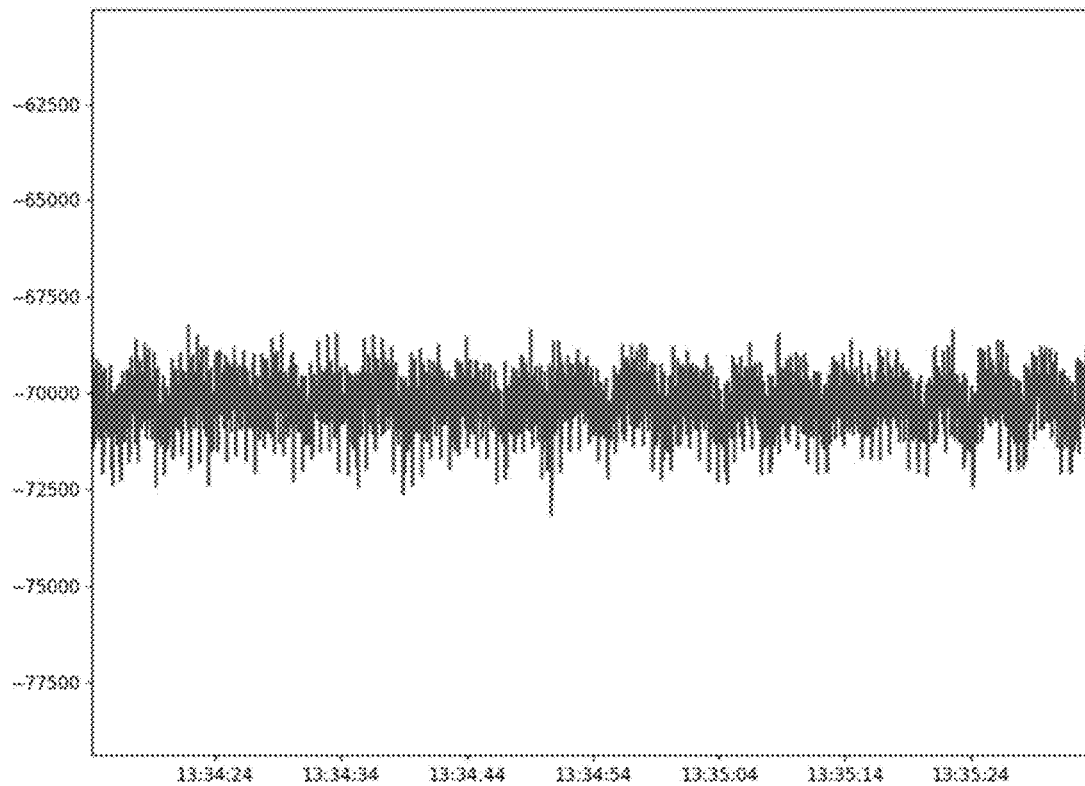
FIG. 7B illustrates an exemplary signal from the piezoelectric sensor, with a bed fan turned off.

FIGS. 7A and 7B illustrate the significant impact that a bed fan or similar noise source has on the data received from a piezoelectric sensor. As can be seen in FIG. 7A, the noise from the fan in the bed overwhelms the signal, and it is difficult to discern the presence of any useful data. In contrast, when the fan is off, as shown in FIG. 7B, it is easy to discern the heart rate pulses (the prominent spikes) in the periodic undulation of approximately 5 second period of respiration. By supplementing the real-time measurements with environmental noise impacts with the sampled data without those noise sources, a more accurate determination of sleep parameters can be made. Therefore, noise source controller 240 can be used to turn off noise sources. In one embodiment, this is done periodically, to build a baseline of data without the noise. In one embodiment, this is done after an event is detected, which should be verified.

The user side elements 210 further include a communication logic 247 to send data to the analysis engine 250. In one embodiment, the communication logic 247 also may send instructions to the user side elements 210. In one embodiment, the analysis engine 250 determines when the controllable noise sources should be turned off, to either set a baseline or validate an identified event. In one embodiment, the communication logic 247 is also used to communicate between the receiver associated with the system and the user's mobile device or other device which is used to interface the user with the system.

The user interface 245 in one embodiment includes basic user interface features on the receiver. These basic user interface features may include one or more buttons and/or LEDs, or a small display screen. In one embodiment, the user side elements 210 further include a mobile application running on the user's mobile device, which interfaces with the receiver. Such a mobile application provides a better user interface 245 enabling the user to see the collected data and results of the associated analysis.

The analysis engine 250 in one embodiment is a computer including a processor and memory, or a plurality of processors and distributed memories.

The analysis engine 250 includes a sender/receiver 255 to receive data from the user side elements 210, and send data to the user side elements 210. In one embodiment, the receiver/sender 255 sends data to the user's mobile device as well, and receives data from the user's mobile device.

The analysis engine 250 includes a buffer and memory 260, to store data from the user side elements. This data, in one embodiment, is preprocessed data. In one embodiment, this is raw data. In one embodiment, the communications logic 247 sends both types of data, and both are stored in memory 260.

Sleep characteristic logic 265 analyzes the data from the sensors, to identify various sleep characteristics. Sleep characteristics 265 include sleep phase, sleep position, sleep sounds, sleep events such as apnea events, or snoring events.

User side element controls 270 send control signals to the user side elements. In one embodiment, those control signals may include signals to adjust the bed configuration, to turn on or off noise sources, to adjust how frequently the sensor collects data, how frequently sensor data is sent to the analysis engine 250, etc.

Base level identifiers 275 identify base level of signals for various configurations. Base levels, in one embodiment, are a baseline signal which is received under various circumstances when there is no sleep event occurring. In one embodiment, the system identifies a plurality of baseline levels, for various configurations of the bed and the controllable noise sources.

Continuous updating logic 280 continuously updates the baseline data, as additional data is received. In one embodiment, the continuous updating logic 280 reprocesses the data as new information is received, to have accurate baseline information about the environment and the user.

Adaptive timers 285 set timing for the noise source controller to turn off the controllable noise sources. The adaptive timers in one embodiment set timing based on a likelihood that sleep sounds or sleep events have been detected. In one embodiment, the adaptive timers 285 are adjusted based on a variety of factors including sleep position, sleep phase, sensor data, and/or analyzed sleep sound data. In one embodiment, the adaptive timers 285 further are adjusted based on this user's analyzed data results. For example, while all users are more likely to snore or have apnea events while sleeping on their back, some users may have a significant impact on their sleep sounds based on season, temperature, time of day, and other factors. In one embodiment, the adaptive timers 285 may adjust the timing for turning off the noise sources based on such additional factors. In one embodiment, adaptive timers 285 may also take into account the potential impact of turning off the noise sources on the user's sleep quality. For example, suddenly turning off a white noise machine when the user is in a light sleep phase may trigger the user to wake, which may not be a good outcome. Therefore, in one embodiment, the adaptive timers 285 may adjust the timing of such actions to maximize the ability to detect sleep events, and minimize the disruption to the user's sleep.

Confidence interval logic 290 assigns a confidence interval for the identification of sleep events, and determines whether the confidence interval is above a threshold. In one embodiment, the system has a base threshold between 75% and 95% to minimize false positives and false negatives. If the accuracy/confidence interval is not above the threshold, the system continues to sample the data. In one embodiment, this process may exit if after a set number of samplings no increase in accuracy are obtained.

Adjustor and alert systems 295 in one embodiment, utilize the determinations of the analysis engine 250 to send control signals to the user side elements 210. In one embodiment, the control signals may be used to adjust the environment of the user. For example, the bed may be adjusted to address a sleep issue detected. In one embodiment, the system may adjust one or more of the bed configurations, including angles of bed parts, temperature, air flow, etc., or exterior systems including the white noise machine, thermostat, lights, etc. In one embodiment, the adjustor and alert system 295 may also be used to adjust the system to enhance the user's sleep, even if no sleep event is detected. For example, a user hovering on the edge of deep sleep may do better if the temperature is lowered. The system may therefore utilize the adjustor and alert system 295 to lower the ambient temperature of the room in which the user is sleeping.

In one embodiment, the control signals may be used to send an alert to wake the user, or to trigger them to adjust their sleep position to address a detected issue. In one embodiment, the alert system may send an alert to a third party, if necessary.

Figure 3:
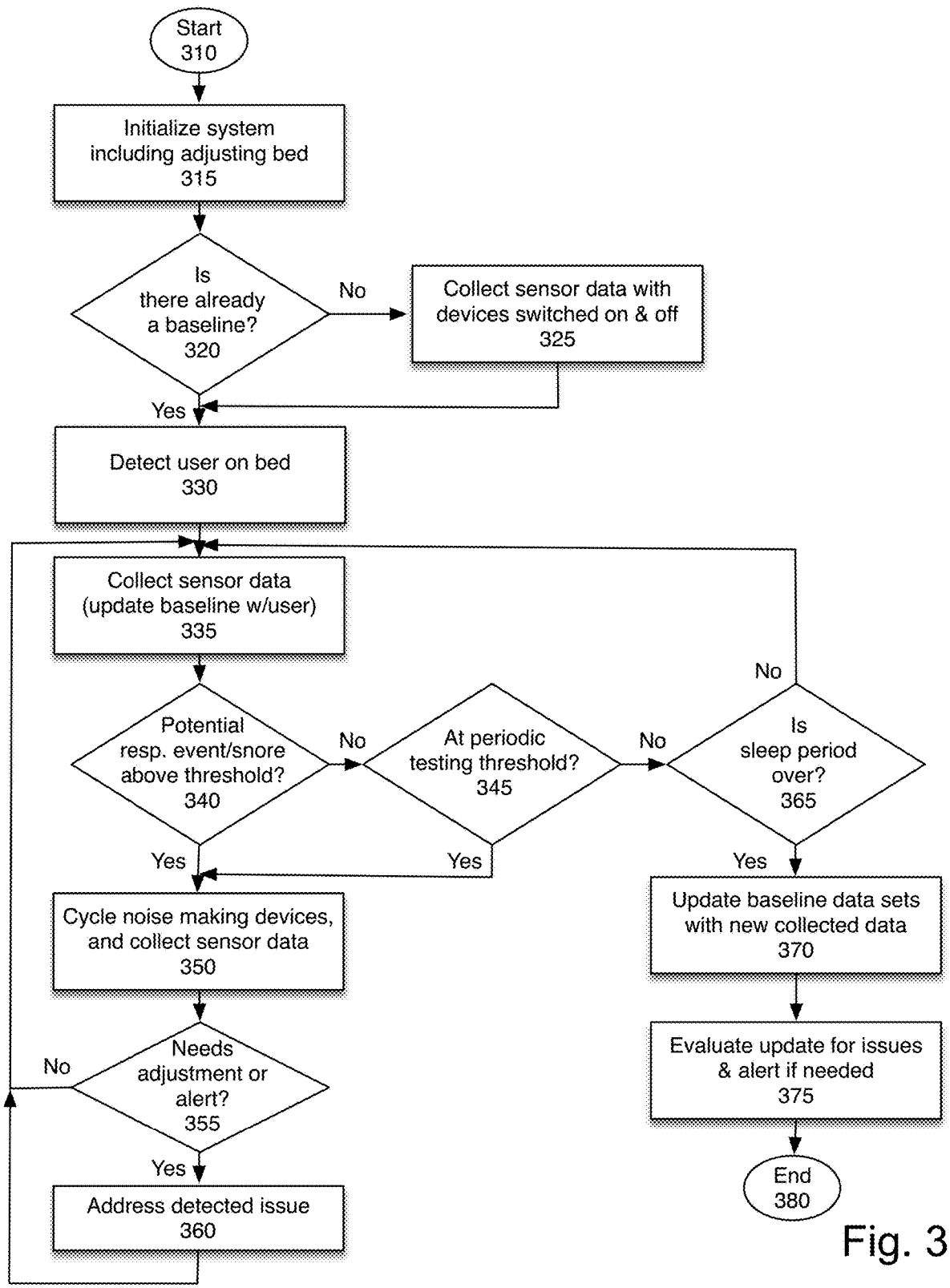
FIG. 3 is an overview flowchart of one embodiment of using the sleep noise detection system.

FIG. 3 is an overview flowchart of one embodiment of using the sleep noise detection system. The process starts at block 310. In one embodiment, the process starts when the sensor system is activated. In one embodiment, this may be after it is initially set up, or after it has been unplugged, or powered down.

At block 315, the process initializes the sleep noise detection system. In one embodiment, this includes ensuring that the connections between the sensor and the receiver, and the controller and the receiver, and any IoT systems have been successfully established. In one embodiment, initialization further includes adjusting the bed to a baseline position if the bed is unoccupied. In one embodiment, for a configurable bed, the default position may be flat. In one embodiment, the default position may be the user's default position if that is known. Many users find a bed configuration they prefer, and then program that as their default position.

At block 320, the process determines whether there is already a baseline for the system. A baseline is a prior analyzed data set of the noise profile of the sleeping area including the bed adjustment parts, IoT controlled noise sources, and uncontrolled noise sources. In one embodiment, the baseline depends on the location of the user, e.g. if the user is in a new room, or new house, the system needs to set a new baseline, because it will have different environmental sound factors. In one embodiment, the system utilizes a movement sensor to determine whether the system has been physically moved to a new location. If so, in one embodiment, the system resets the baseline for the environmental factors. In one embodiment, global positioning system (GPS) or other location data is used to determine whether the system has been moved. In one embodiment, the location data may be obtained from the user device associated with the system.

If there is no existing baseline, which in one embodiment means that the sensor system was either newly initialized or moved since a baseline was set up, at block 325 sensor data is collected with devices switched on and off. In one embodiment, sensor data may be collected for a variety of available configurations of the noise sources as well as the bed geometry. For example, in a system in which the bed has a heater, and a cooler, and the bed geometry may include a raised head, and raised feet, and there is a separate white noise machine, the following sets of data may be collected as part of the baseline:

For each bed configuration:
baseline sound value with heater on/off, no user on bed
baseline sound value with heater on/off, user on bed
baseline sound value with cooler on/off, no user on bed
baseline sound value with cooler on/off, user on bed
baseline sound value with fan at setting 1, 2, 3, n, no user on bed
baseline sound value with fan at setting 1, 2, 3, n, user on bed
baseline sound value with motor on/off, no user on bed
baseline sound value with motor on/off, user on bed
baseline sound value with white noise machine on/off, no user on bed
baseline sound value with white noise machine on/off, user on bed In one embodiment, the system further evaluates baselines for the various combinations of the above. Of course, if there are additional noise sources those can also be taken into account. In one embodiment, the baselines are built up over time. The process then continues to block 330. If there are existing baselines, the process continues directly to block 330.

At block 330, the process detects the user on the bed. In one embodiment, a pressure sensor or similar simple sensor is used to detect the user's presence on the bed. In one embodiment, in response to this detection the sample rate of the sensors is increased to collect user data.

At block 335, sensor data is collected. In one embodiment, if no baseline data is yet present, the baseline data is updated with the user on the bed. In one embodiment, this is done when the user is not yet asleep, to ensure that there are no sleep sounds (e.g. apneas and snoring).

At block 340, the process determines whether a potential snore or respiratory event is detected, and if so, whether the potential is above a threshold. In one embodiment, the analysis of the sensor data enables the system to extract heartrate, respiration, as well as apnea and snore data (when present). Such data is assigned a probability, in one embodiment, ranging between 1% and 99%. In one embodiment, if the probability that a snore is detected is above 50% (or 75%) the process continues to block 350. Otherwise, the process, at block 345 determines whether it is time to collect sensor data, for accuracy. In one embodiment, the system periodically performs such a test even if the potential of a sleep sound is below the threshold. If it is time for testing, the process continues to block 350.

If it is not time for testing, at block 365 the process determines whether the sleep period is over. If not, the process returns to block 335 to continue collecting sensor data. If the sleep period is over, at block 370 the baseline data sets are updated based on the analyzed new collected data, in one embodiment. By continuously updating the baseline, the system can evaluate these updates to determine whether they are indicative of an issue, and if necessary, at block 375 triggering an alert. The process then ends at block 380.

If the system determines that it's time to do a more controlled analysis, because the potential respiratory event/snore threshold is above a limit, or a timer indicates that it should be done, the process at block 350 cycles the noise making devices and collects sensor data. In one embodiment, the cycling of noise making devices attempts to eliminate the extraneous noise sources for more accurate recording. In one embodiment, the cycling may be rapid enough to not impact the temperature or other controls. In one embodiment, the cycle time may be sub-5-seconds. In one embodiment, the cycle time may be between 1 second and 30 seconds. In one embodiment, the length of the cycle may depend on the evaluation of the collected data.

At block 355, the process determines whether this more accurate data indicates that an adjustment should be made, or an alert sent. If so, the detected issue is addressed, at block 360. The process then returns to continue collecting sensor data.

Of course, though this is shown as a flowchart, in one embodiment it is implemented as an interrupt-driven system, such that the data collection is continuous, and the evaluation is triggered by timers and interrupts. Additionally, the ordering of the evaluations checking is arbitrary. For this flowchart, and the below flowchart, unless the processes are dependent on each other, the ordering of the blocks in the flowchart may be altered, without departing from the invention.

Figure 4:
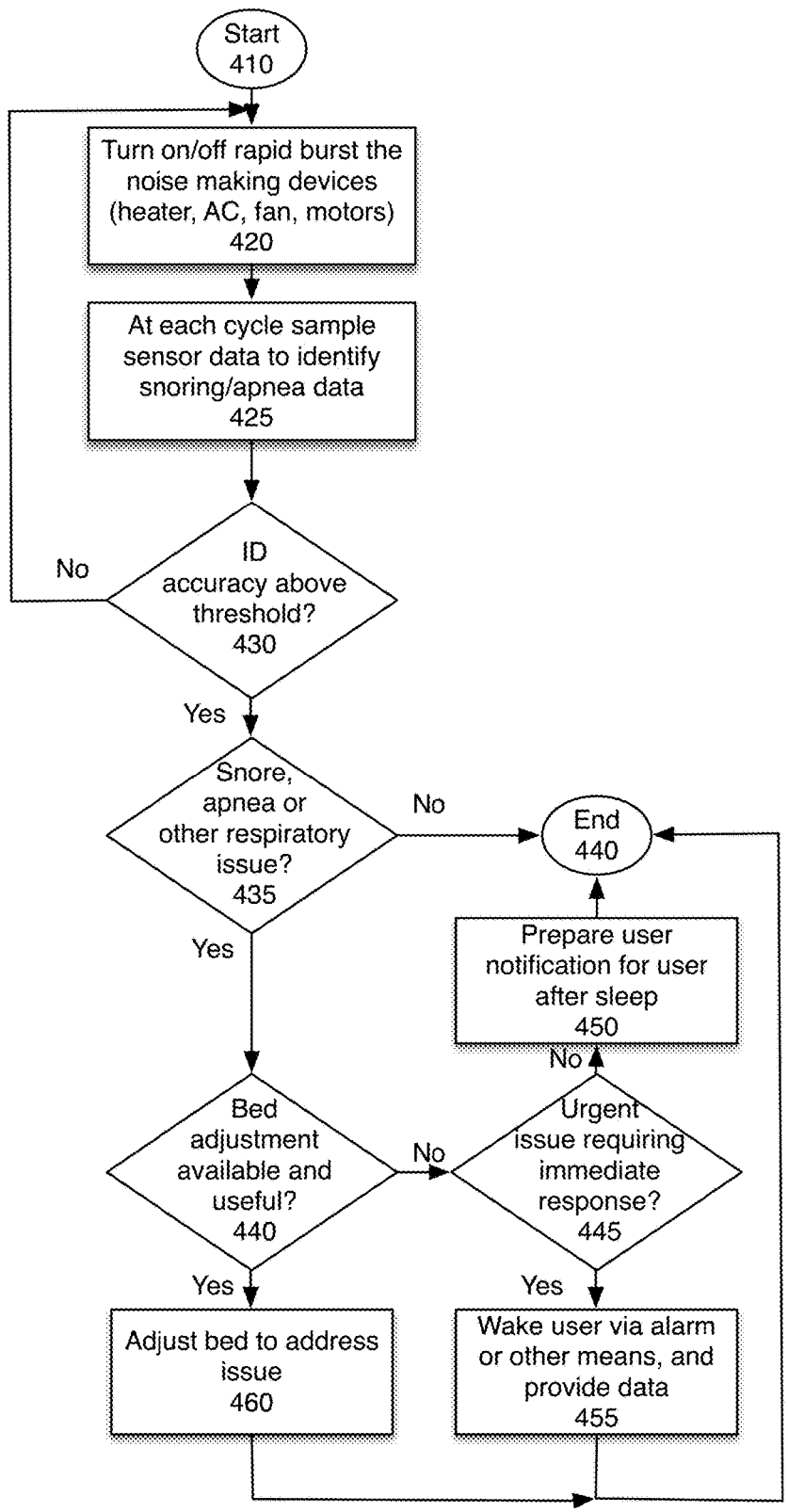
FIG. 4 is a flowchart of one embodiment of a detection cycle.

FIG. 4 is a flowchart of one embodiment of a detection cycle. The process starts at block 410. In one embodiment, this process corresponds to blocks 350-360 in FIG. 3.

Returning to FIG. 4, at block 420, the system turns on/off in rapid burst the noisemaking devices in the environment that can be controlled by the system. This includes the bed adjustment parts as well as IoT controlled noise sources, in one embodiment. At each cycle, at block 425, the sensor data is sampled to obtain "clean" sensor data without influence from external noise sources. In one embodiment, the cycling of these systems is rapid enough that the user should not experience any changes in their sleep environment as a result. In one embodiment, if there are noise sources which are not controlled (for example central heating or cooling in the room) in one embodiment, the system determines when such noise sources are off, and times the cycling during those periods. The system uses the sampled sensor data to identify sleep sounds, including apneas and/or snoring. In one embodiment, the identification is assigned a confidence interval.

At block 430, the process determines whether the confidence interval for the identification is above a threshold. In one embodiment, the system has a base threshold between 75% and 95% to minimize false positives and false negatives. If the accuracy/confidence interval is not above the threshold, the system continues to sample the data. In one embodiment, this process may exit if after a set number of samplings no increase in accuracy are obtained. For example, if the accuracy does not increase above the prior threshold after three additional samples, the process may go directly to block 435, even if the confidence interval is below the threshold.

At block 435, the process determines whether a sleep sound was identified. The sleep sound may be indication of an apnea, snoring, or another respiratory issue. For example, mouth breathing may be identified as well.

If no such issue is identified, this process ends at block 440. This means the process returns to block 335, to continue monitoring.

If an issue is identified, the process determines at block 440 whether a bed adjustment is available and useful in this situation. If so, at block 460 the bed is adjusted. For example, for snoring, it is known that raising the bed can stop someone from snoring. Similarly, for apnea it is known that turning to the side can improve such breathing issues.

Therefore, a bed adjustment, if available, may be used to resolve the issue. The process then ends.

If a bed adjustment is not available and/or not useful, at block 445 the process determines whether the issue is urgent requiring immediate attention. If so, at block 455 the user may be woken via an alarm and may be alerted to the issue. In one embodiment, this path is only taken if failing to wake the user may result in endangering the user's health. Otherwise, a user notification is prepared to inform the user after sleep, at block 450. The process then ends.

Figure 5:
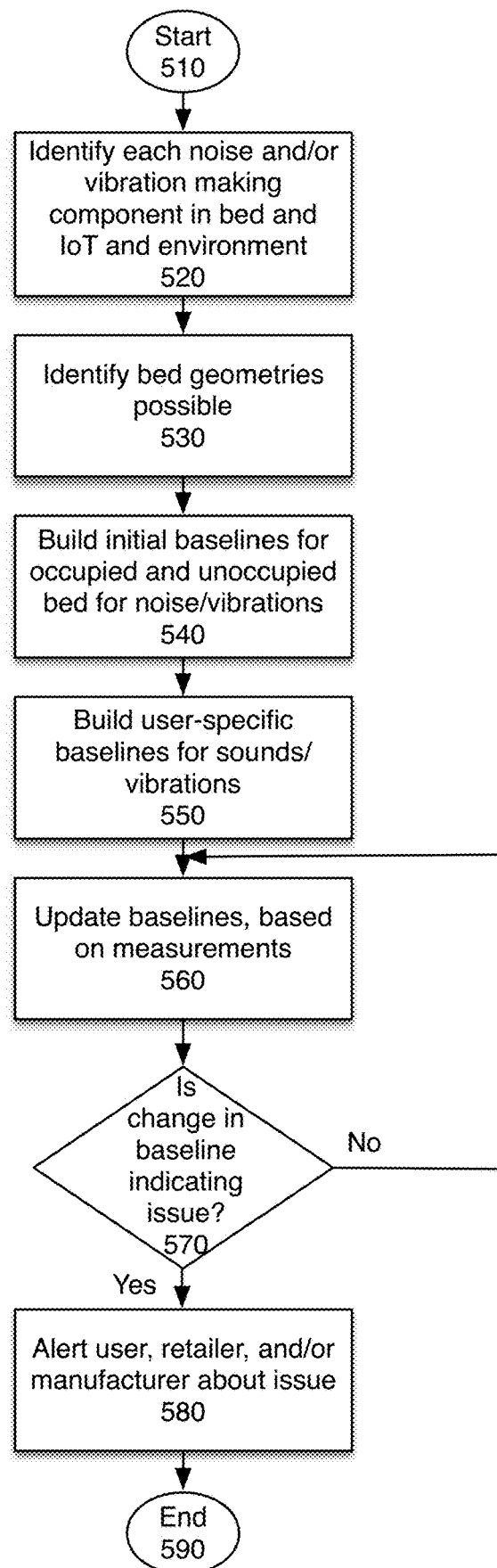
FIG. 5 is a flowchart of one embodiment of updating baselines.

FIG. 5 is a flowchart of one embodiment of updating baselines. The process starts at block 510.

At block 520, each noise source (e.g. system within the sleep environment that makes noise or other vibrations) is identified. In one embodiment, this includes in-bed devices and external IoT devices. In one embodiment, this may also include external non-IoT devices, which are either identified by the user, or identified based on their signal.

At block 530, the bed geometries are identified. In one embodiment, bed geometries include the configurations of the bed. In one embodiment, for a smoothly moving bed which may have thousands of configurations, a set-wise set of possible geometries are identified. In one embodiment, the set of geometries are constrained by the geometries used by the user. That is, if the user does not for example ever elevate the foot of the bed higher than the head of the bed, those geometries may be excluded from further evaluation.

At block 540, the initial baselines are built for the occupied and unoccupied bed for noise/vibrations. As noted above, this may be done by cycling the various noise sources individually, and in combination.

At block 550, in one embodiment, user specific baselines are set. In one embodiment, the user specific baselines include the user's impact on the bed and may be different for each user occupying the bed. In one embodiment, a user specific baseline also includes the user's standard heartrate, respiration, and sleep sounds as recorded over the sleep cycle.

At block 560, the process updates the baselines, based on sensor data collected. In one embodiment, updating occurs after each sleep session. In one embodiment, updating occurs after a certain number of sleep sessions. In one embodiment, updating only occurs when the difference between the baseline and the currently recorded data is above a threshold.

At block 570, the process determines whether the change in the baseline indicates a potential issue. In one embodiment, a potential issue may be a potential issue for the user, e.g. the pattern of change over time in the user's heart rate, respiration, or sleep sounds indicates that the user is developing a problem, such as sleep apnea or even just a sinus infection which changes the user's breathing. The potential issue may be one for the noise sources, e.g. the motors in the bed or coils in the cooler becoming less efficient.

At block 580, the appropriate entity is alerted about the potential issue. In one embodiment, the user may be alerted about his or her own sleep pattern changes which indicates a potential problem. In one embodiment, the user may be alerted about issues with the noise sources as well. The alert may suggest for example that the user replace the motor or clean the coils. In one embodiment, the alert may also be to a retailer and/or manufacturer, as appropriate. For example, if the system is under warranty, the manufacturer may be alerted that a warranty service should be scheduled or that a replacement part should be sent. In one embodiment, cumulative data over time may also be provided to a manufacturer. This is useful in monitoring the performance of high-end beds over time in real-world environments. The process then ends at block 590.

Figure 6:
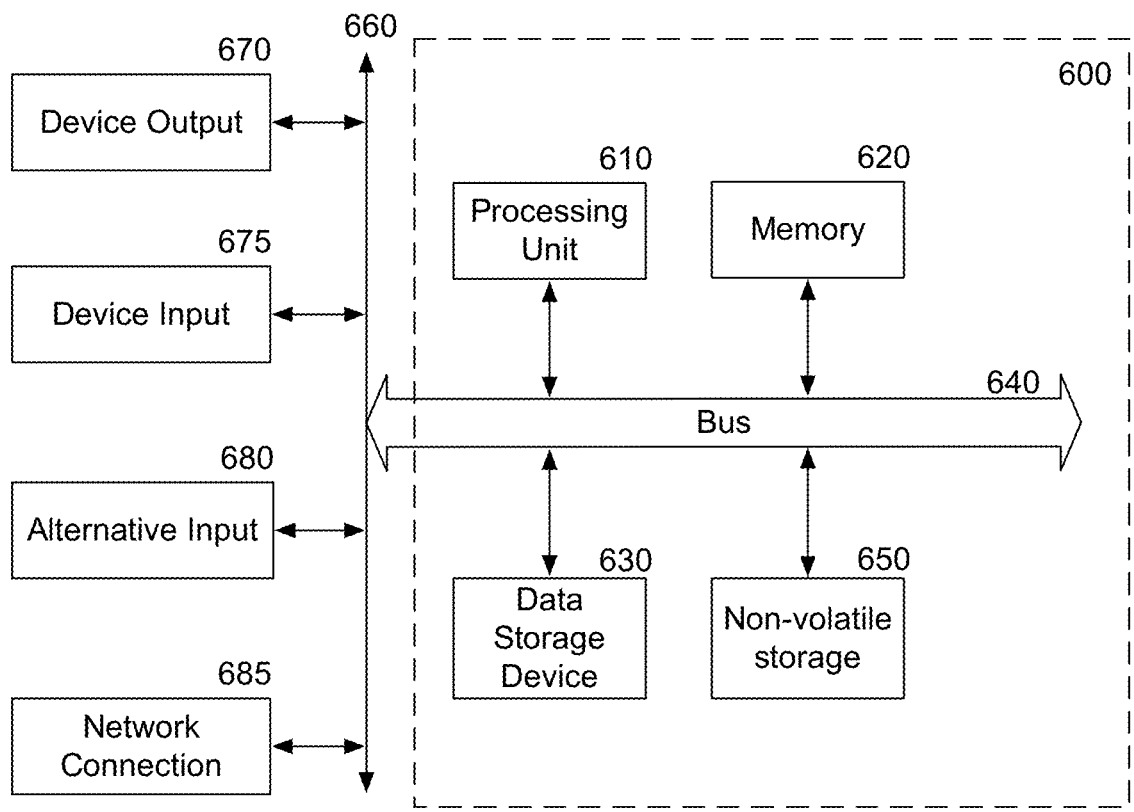
FIG. 6 is a block diagram of one embodiment of a computer system which may be used with the present system.

FIG. 6 is a block diagram of one embodiment of a computer system that may be used with the present invention. It will be apparent to those of ordinary skill in the art, however that other alternative systems of various system architectures may also be used.

The data processing system illustrated in FIG. 6 includes a bus or other internal communication means 640 for communicating information, and a processing unit 610 coupled to the bus 640 for processing information. The processing unit 610 may be a central processing unit (CPU), a digital signal processor (DSP), or another type of processing unit 610.

The system further includes, in one embodiment, a random-access memory (RAM) or other volatile storage device 620 (referred to as memory), coupled to bus 640 for storing information and instructions to be executed by processor 610. Main memory 620 may also be used for storing temporary variables or other intermediate information during execution of instructions by processing unit 610.

The system also comprises in one embodiment a read only memory (ROM) 650 and/or static storage device 650 coupled to bus 640 for storing static information and instructions for processor 610. In one embodiment, the system also includes a data storage device 630 such as a magnetic disk or optical disk and its corresponding disk drive, or Flash memory or other storage which is capable of storing data when no power is supplied to the system. Data storage device 630 in one embodiment is coupled to bus 640 for storing information and instructions.

The system may further be coupled to an output device 670, such as a cathode ray tube (CRT) or a liquid crystal display (LCD) coupled to bus 640 through bus 660 for outputting information. The output device 670 may be a visual output device, an audio output device, and/or tactile output device (e.g. vibrations, etc.)

An input device 675 may be coupled to the bus 660. The input device 675 may be an alphanumeric input device, such as a keyboard including alphanumeric and other keys, for enabling a user to communicate information and command selections to processing unit 610. An additional user input device 680 may further be included. One such user input device 680 is cursor control device 680, such as a mouse, a trackball, stylus, cursor direction keys, or touch screen, may be coupled to bus 640 through bus 660 for communicating direction information and command selections to processing unit 610, and for controlling movement on display device 670.

Another device, which may optionally be coupled to computer system 600, is a network device 685 for accessing other nodes of a distributed system via a network. The communication device 685 may include any of a number of commercially available networking peripheral devices such as those used for coupling to an Ethernet, token ring, Internet, or wide area network, personal area network, wireless network, or other method of accessing other devices. The communication device 685 may further be a null-modem connection, or any other mechanism that provides connectivity between the computer system 600 and the outside world.

Note that any or all of the components of this system illustrated in FIG. 6 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 620, mass storage device 630, or other storage medium locally or remotely accessible to processor 610.

It will be apparent to those of ordinary skill in the art that the system, method, and process described herein can be implemented as software stored in main memory 620 or read only memory 650 and executed by processor 610. This control logic or software may also be resident on an article of manufacture comprising a computer readable medium having computer readable program code embodied therein and being readable by the mass storage device 630 and for causing the processor 610 to operate in accordance with the methods and teachings herein.

The present invention may also be embodied in a handheld or portable device containing a subset of the computer hardware components described above. For example, the handheld device may be configured to contain only the bus 640, the processor 610, and memory 650 and/or 620.

The handheld device may be configured to include a set of buttons or input signaling components with which a user may select from a set of available options. These could be considered input device #1 675 or input device #2 680. The handheld device may also be configured to include an output device 670 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 610, a data storage device 630, a bus 640, and memory 620, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals but may be configured and accessed through a website or other network-based connection through network device 685.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 610. A machine-readable medium includes any mechanism for storing information in a form readable by a machine (e.g. a computer). For example, a machine-readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical, or other forms of propagated signals (e.g., carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A system of monitoring sleep in a sleep environment, the system comprising:
   a sensor;
   a noise source controller to identify one or more uncontrolled noise sources in the sleep environment, and determine when the one or more uncontrolled noise sources are at a baseline level;
   a data collector triggered by the noise source controller to collect sensor data from the sensor when the uncontrolled noise sources are at the baseline level, the sensor data used to determine a user's sleep parameters, including sleep sounds; and
   a sleep sound logic to use the sensor data to determine the user's sleep parameters.

2. The system of claim 1, wherein use of the noise source controller reduces false positives and false negatives.

3. The system of claim 1, further comprising:
   the noise source controller to cycle one or more external controlled noise sources off and on.

4. The system of claim 3, wherein the noise source controller is configured to cycle the one or more external controlled noise sources when the uncontrolled noise sources are at the baseline level.

5. The system of claim 3, further comprising:
   adaptive timers to set timing for the noise source controller to cycle the external controlled noise sources, the adaptive timers setting the timing based on a likelihood that the sleep sounds have been detected.

6. The system of claim 3, wherein the noise source controller cycles the external controlled noise sources in a rapid burst, so that the user's sleep is not disrupted.

7. The system of claim 1 further comprising:
   the data collector collecting data from the sensor under a plurality of noise levels;
   a baseline level identifier to calculate one or more baselines for the data from the sensor under various circumstances; and
   the sleep sound logic to use the baseline to determine whether there is a potential respiratory event.

8. The system of claim 7, further comprising:
   the baseline level identifier to update a current baseline based on the data.

9. The system of claim 1, further comprising:
   a user side element control to send control signals to adjust a bed configuration.

10. The system of claim 1, wherein the baseline level for the uncontrolled noise sources is off.

11. A system of monitoring sleep in a sleep environment, the system comprising:
    a sensor;
    a noise source controller to identify one or more uncontrolled noise sources in the sleep environment, and determine when the one or more uncontrolled noise sources are off;
    a data collector triggered by the noise source controller to collect sensor data from the sensor when the uncontrolled noise sources are off, the sensor data used to determine a user's sleep parameters, including sleep sounds; and
    a sleep sound logic to use the sensor data to determine the user's sleep parameters.

12. The system of claim 11, wherein use of the noise source controller reduces false positives and false negatives.

13. The system of claim 11, further comprising:
the noise source controller to cycle one or more external controlled noise sources off and on.

14. The system of claim 13, wherein the noise source controller is configured to cycle the one or more external controlled noise sources when the uncontrolled noise sources are off.

15. The system of claim 13, further comprising:
adaptive timers to set timing for the noise source controller to cycle the external controlled noise sources, the adaptive timers setting the timing based on a likelihood that the sleep sounds have been detected.

16. The system of claim 13, wherein the noise source controller cycles the external controlled noise sources in a rapid burst, so that the user's sleep is not disrupted.

17. The system of claim 11 further comprising:
the data collector collecting data from the sensor under a plurality of noise levels;
a baseline level identifier to calculate a baseline for the data from the sensor under various circumstances; and
the sleep sound logic to use the baseline to determine whether there is a potential respiratory event.

18. The system of claim 17, further comprising:
the baseline level identifier to update the baseline based on the data.

19. The system of claim 11, further comprising:
a user side element control to send control signals to adjust a bed configuration.

20. A method of monitoring sleep in a sleep environment, the method comprising:
identifying one or more uncontrolled noise sources in the sleep environment, and determining when the one or more uncontrolled noise sources are at a baseline level;
triggering a data collector to collect sensor data from a sensor when the uncontrolled noise sources are at the baseline level, the sensor data used to determine a user's sleep parameters, including sleep sounds; and
determining the user's sleep parameters using the sensor data.

\* \* \* \* \*